(12) United States Patent
Sethi

(10) Patent No.: US 7,179,469 B2
(45) Date of Patent: Feb. 20, 2007

(54) BENEFICIAL EFFECT OF DISTILLER'S GRAIN IN CARDIOVASCULAR DISEASE

(76) Inventor: Rajat Sethi, 3 Bunton Court, Winnipeg Manitoba (CA) R3X 1K4

( * ) Notice: Subject to any disclaimer, the term of this patent is extended or adjusted under 35 U.S.C. 154(b) by 8 days.

(21) Appl. No.: 10/834,915

(22) Filed: Apr. 30, 2004

(65) Prior Publication Data
US 2004/0234630 A1 Nov. 25, 2004

Related U.S. Application Data

(60) Provisional application No. 60/492,993, filed on Aug. 7, 2003, provisional application No. 60/471,363, filed on May 19, 2003, provisional application No. 60/466,782, filed on May 1, 2003.

(51) Int. Cl.
*A61K 36/00* (2006.01)
(52) U.S. Cl. .................... 424/195.16; 424/750
(58) Field of Classification Search ........... 424/195.16, 424/750
See application file for complete search history.

(56) References Cited

U.S. PATENT DOCUMENTS

| 5,177,008 A | | 1/1993 | Kampen | |
|---|---|---|---|---|
| 5,246,717 A | * | 9/1993 | Garwin | 426/2 |
| 5,439,701 A | * | 8/1995 | Zimlich, III | 426/624 |
| 5,843,499 A | * | 12/1998 | Moreau et al. | 426/2 |

OTHER PUBLICATIONS

Internet website—http://www.chclibrary.org/micromed/00053500.html. 9 pages total.*
Internet website—http://nationalhogfarmer.com/mag/farming_distillers_grains_offers/. 4 pages total.*
Tran, M. "Ischemia," Gale Encyclopedia of Alternative Medicine, 2001. (8 pages total).*
Vetterlein, Friedrich et al, "Extent of damage in ischemic, nonreperfused, and reperfused myocardium of anesthetized rats", *Am J Physiol Heart Circ Physiol*, vol. 285, Aug. 2003; p. H755-H765.
Lapointe, Nathalie et al, "Effects of pre-, peri and postmyocardial infarction treatment with omapatrilat in rats: survival, arrhythmias, ventricular function, and remodeling", *Am J Physiol Heart Circ Physiol*, vol. 285, Jul. 2003; p. H398-H405.
Schingoethe, D. J. et al, "Milk production and composition from cows fed wet corn distillers grains", *J Dairy Sci*, vol. 82, No. 3, 1999; p. 574-580.
Grings, E. E. et al, "Response of dairy cows to additions of distillers dried grains with solubles in alfalfa-based diets", *J Dairy Sci*, vol. 75, No. 7, 1992; p. 1946-1953.
Ham, G. A. et al, "Wet corn distillers byproducts compared with dried corn distillers grains with solubles as a source of protein and energy for ruminants", *J Anim Sci.*, Dec. 72(12) 1994; p. 3246-3257.

(Continued)

*Primary Examiner*—Christopher Tate
*Assistant Examiner*—S. B. McCormick-Ewoldt
(74) *Attorney, Agent, or Firm*—Michael R. Williams; Adrian D. Battison; Ryan W. Dupuis

(57) ABSTRACT

The use of a food portion comprising dry and/or wet distiller's grain for preventing, treating or ameliorating cardiovascular pathologies is described.

8 Claims, 5 Drawing Sheets

OTHER PUBLICATIONS

Mahgoub, Mahmoud A. et al, "Diabetes mellitus and cardiac function", *Molecular and Cellular Biochemistry*, 180, 1998; p. 59-64.

Meldrum, K. K. et al, "A novel model of Ischemia in Renal Tubular cells which closely parallels *in vivo* injury", *Journal of Surgical Research*, 99, 2001; p. 288-293.

* cited by examiner

A

B

BENEFICIAL EFFECT OF DISTILLER'S GRAIN IN CARDIOVASCULAR DISEASE

PRIOR APPLICATIONS

The instant application claims priority on U.S. Ser. No. 60/466,782, filed May 1, 2003; U.S. Ser. No. 60/471,363, filed May 19, 2003; and U.S. Ser. No. 60/492,993, filed Aug. 7, 2003.

FIELD OF THE INVENTION

The present invention relates generally to the field of nutritional supplements. More specifically, the present invention relates to a feed supplement.

BACKGROUND OF THE INVENTION

Death as a result of cardiac arrhythmia is an increasing concern in feedlots, especially in fast-growing livestock. Given that most feedlots operate on a slim profit margin, losses of livestock are devastating. Many treatments have been proposed, including supplementing feed with calcium or omega-3 fatty acids.

Distiller's grain by-products are the residual mash remaining after the starch has been extracted, converted to sugar and fermented into ethanol and carbon dioxide. Wet distiller's grain is a whole stillage product, with 10–20% solids. It consists of the entire solids and water left after the alcohol has been removed from the mash but is costly to transport and has a short shelf life. Dry distiller's grain (DDG) is typically prepared by drying wet distiller's grain.

U.S. Pat. No. 6,355,456 teaches an integrated process for fermenting grain to produce ethanol and then feeding the by-product of wet distiller's grain to livestock, among other steps. This reference also teaches feeding high saturation wet distiller's grain with solubles to eliminate acidosis in beef cattle, as well as for improving health and milk/meat quality of dairy cows and beef cattle.

U.S. Pat. No. 5,177,008 teaches a method of producing glycerol as a co-product of ethanol fermentation.

Previously, distiller's grain has been fed to lactating dairy cattle, for example, in place of corn grain or soybean meal and was found to increase milk fat production (Al-Suwaiegh et al., 2002, J. Anim. Sci. 80: 1105–1111). It has also been reported that dried distillers grains are beneficial in some ruminant diets due to their high content of undegraded intake protein (UIP) (Peter et al., 2000, J. Anim. Sci. 78: 1–6). It was proposed that replacing corn in the diet of finishing sheep and cattle with distillers byproducts may help control subacute acidosis on the basis that high starch intake leads to increased production of ruminal organic acids, which in turn may cause reductions in gain and efficiency (Lodge et al., 1997, J. Anim. Sci. 75: 44–50). However, distiller's grain is known to be high in long-chain unsaturated fatty acids which, for example, increase the amounts of $C_{18:0}$ and $C_{18:1}$ in milk fat when fed to dairy cows (Schingoethe et al., 1999, J. Dairy Sci. 82: 574–580).

SUMMARY OF THE INVENTION

According to a first aspect of the invention, there is provided a method of treating, preventing or ameliorating a cardiovascular pathology in an animal comprising:

administering to the animal in need of such treatment a food supplement including distiller's grain.

The distiller's grain may be dry distiller's grain or wet distiller's grain.

The animal may be a livestock animal.

The cardiovascular pathology may be selected from the group consisting of arrhythmia, hypertension, hypertrophy, ischaemia and heart failure, for example, myocardial infarction, ischemic infarction and congestive heart failure.

DESCRIPTION OF THE PREFERRED EMBODIMENTS

Figure 1:
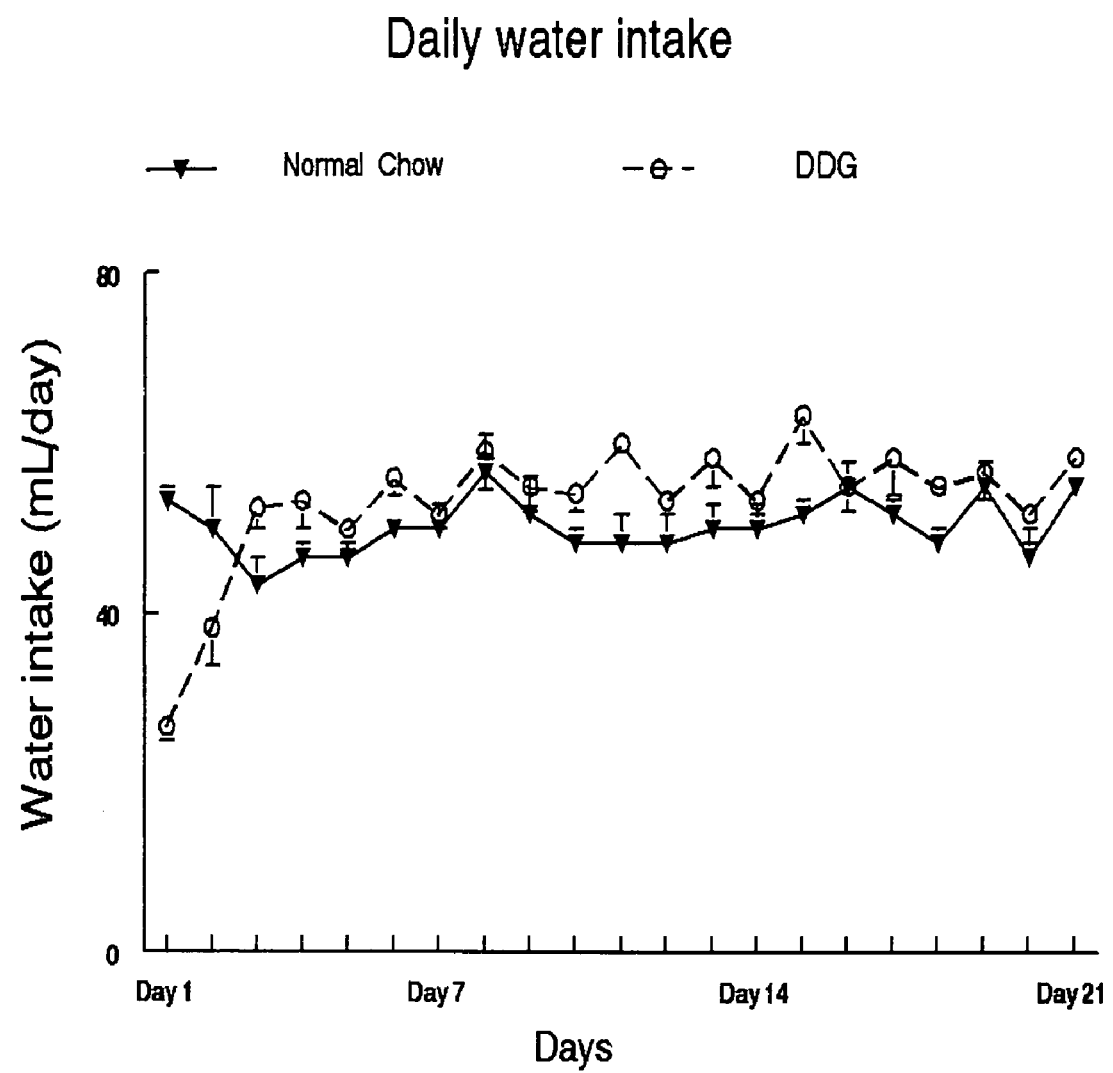
FIG. 1—shows the daily water intake of rats fed normal chow (control, ▼), and rats fed DDG (DDG, ○) (N=3). Data is shown in Table 1.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is the use of distiller's grain, for example dry and/or wet distiller's grain, as a food supplement for a animal, for example, humans, livestock, poultry or fish, for example, although by no means limited to feeder cattle, feeder hogs, broiler chickens, turkeys and fish. As will be apparent to one of skill in the art, these animals are typically bred to be fast-growing or are fed supplements to encourage fast growth. This places considerable strain on the cardiovascular system of the developing animal or human, thereby putting the animal or human at risk of developing any one of a number of cardiovascular pathologies, for example, but by no means limited to arrhythmia, hypertension, hypertrophy, ischaemia and heart failure, as well as cardiovascular pathologies associated with diabetes. As discussed above, cardiac arrhythmia can lead to up to 30% of the livestock in a given feedlot dying prior to slaughter.

Dry distiller's grain has been used as a feed ingredient, typically 30–40% of feeder rations and about 20–30% of dairy rations. As discussed above, wet distillers grain has been shown to be superior to dry distiller's grain.

While distiller's grain has been proposed to be beneficial for animals for treating animals with acidosis or other liver ailments due to its low starch content, it has not previously been proposed that distiller's grain can promote cardiac development, thereby treating or ameliorating or preventing arrhythmia.

It is of note that the distiller's grain may also be fed to individuals or animals suffering from diabetes as a method of treating, ameliorating or preventing diabetes-related cardiovascular pathologies. It is of note that it may be Type I diabetes or Type II diabetes (Mahgoub and Abd-Elfattah, 1998, Mol Cell Biochem 180: 59–64).

While not wishing to be limited or bound to a specific hypothesis, the inventor notes that many cardiovascular pathologies such as arrhythmia are caused by oxidants or by increased calcium influx into the heart. As such, wet and/or dry distiller's grain may act as an anti-oxidant or may act as a calcium channel antagonist, thereby relieving stress on the cardiovascular system of the animal. In view of this, as will be appreciated by one of skill in the art, it is clear that wet and/or dry distiller's grain will be beneficial in a wide variety of animals.

Furthermore, as discussed below, adult rat ventricular myocytes from rats fed a diet of DDG had increased survival when subjected to ischemia using the mineral oil layering induced model of ischemia (Meldrum et al., 2001, Journal of Surgical Research 99: 288–293; Vander Heide et al., 1990, Mol Cell Cardiol 22: 165–181). As noted by Vetterlein et al., 2003, Am J Physiol Heart Circ Physiol 285: H755–H765, even though an ischemic injury may appear reversible, a certain fraction of the myocytes may develop necrosis upon reperfusion. This is consistent with the view that ischemia, which refers to a lack of oxygen due to inadequate perfusion, causes transient disturbances of the mechanical (reduced heart function and heart failure), structural (hypertrophy), biochemical (hypertension) and electrical functions (arrhythmia) of the myocardium. It is also worth noting that the damage upon reperfusion is dependent upon the extent of ischemia. This in turn can lead to other cardiac pathologies, as discussed above. Thus, preventing or protecting myocytes from ischemia will protect the cardiovascular system of an animal from other cardiac pathologies as well.

Moreover, since diabetes is associated with the cardiovascular complications mentioned above, wet and/or dry distiller's grain would be beneficial if administered to individuals having or at risk of developing diabetes.

The wet and/or dry distiller's grain may be prepared from any suitable source, for example, wheat, cereal grains, barley and/or corn.

Dry distiller's grain typically has a moisture content of about 5–8%, protein content of about 25–40%, fibre content of about 7–10%, calcium content of about 0.10–0.15%, phosphorus content of about 0.7–0.95%, potassium content of about 0.4–1.1% and about 250–400 ppm of iron.

In some embodiments, wet and/or dry distiller's grain is used as a food supplement, mixed with, for example, traditional livestock feed, at a ratio between 1 part distiller's grain: 9 parts feed to 3 parts distiller's grain: 1 part feed, inclusive. Furthermore, for humans, wet and/or dry distiller's grain could be incorporated into bakery products, for example, bread, buns and the like, or into other suitable foods, for example, cereal, granola, breakfast or energy bars or the like. As will be appreciated by one of skill in the art, the process of making these food items is well known in the art and wet and/or dry DDG can easily be substituted for one or more of the traditional ingredients.

As discussed above, in some embodiments, wet and/or dry distiller's grain is mixed with a food supplement or food product and an effective dose thereof is administered to an animal at risk of or suffering from at least one cardiovascular pathology, thereby treating or ameliorating or preventing the cardiovascular pathology.

Arrhythmia is a dissociation between atrial and ventricular contractions which in turn raises atrial pressures. Hypertrophy occurs when ventricles respond to a chronically hemodynamic burden by developing an increase in muscle mass. Ischemia refers to a lack of oxygen due to inadequate perfusion which results from an imbalance between oxygen supply and demand. Heart failure is defined as an abnormality of cardiac function caused for example by a reduction in cardiac efficiency and/or alterations in energy metabolism which in turn results in a failure of the heart to pump blood at a rate commensurate with the requirements of the metabolizing tissues. Hypertension refers to increased or elevated arterial pressure. As discussed above, distiller's grain will treat, prevent or ameliorate symptoms associated with these and other cardiovascular pathologies by acting as an anti-oxidant and/or as a calcium channel antagonist, thereby removing stress on the heart and cardiovascular system of the mammal.

Figure 2:
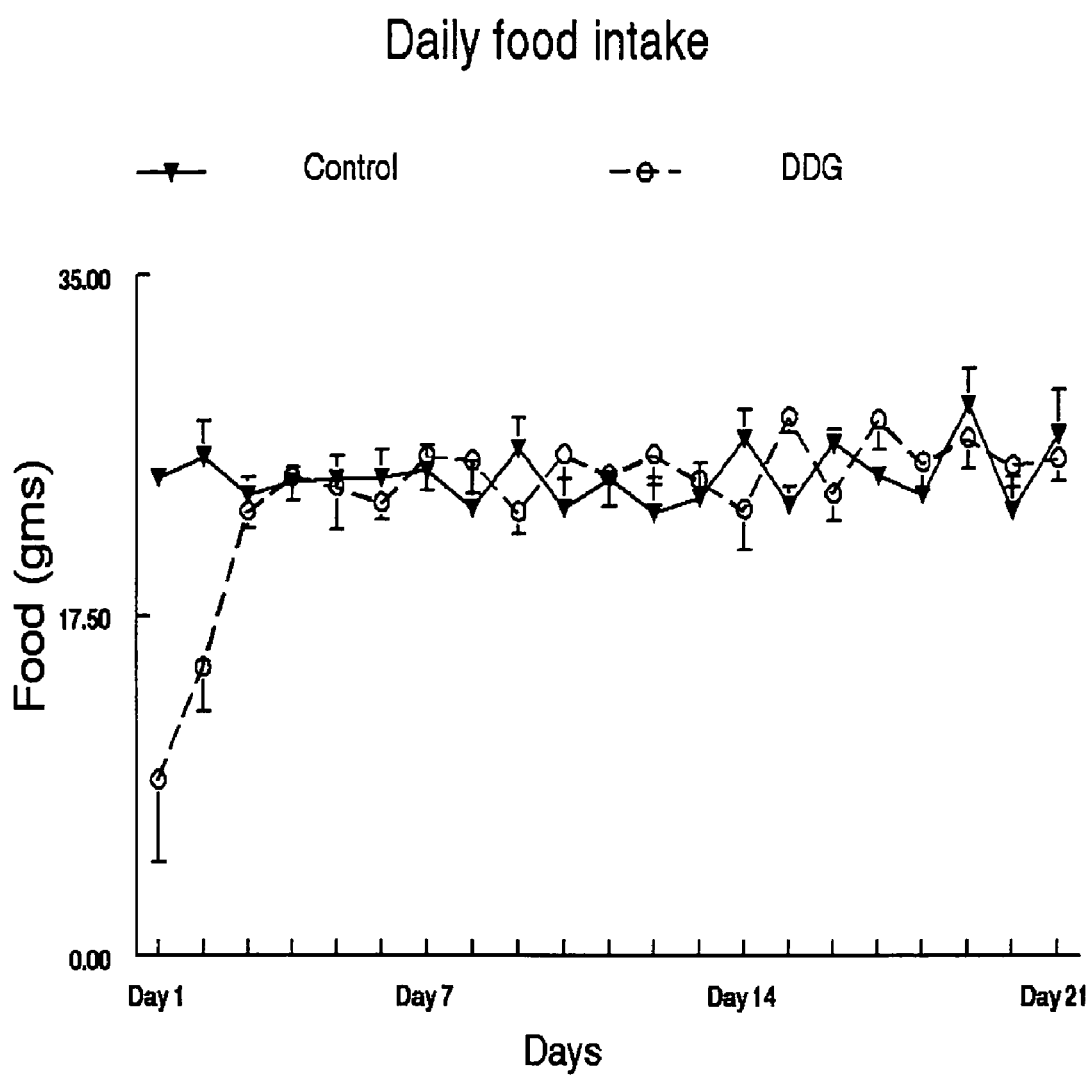
FIG. 2—shows the daily food intake of rats fed normal chow (control, ▼), and rats fed DDG (DDG, ○) (N=3). Data is shown in Table 2.
Figure 3:
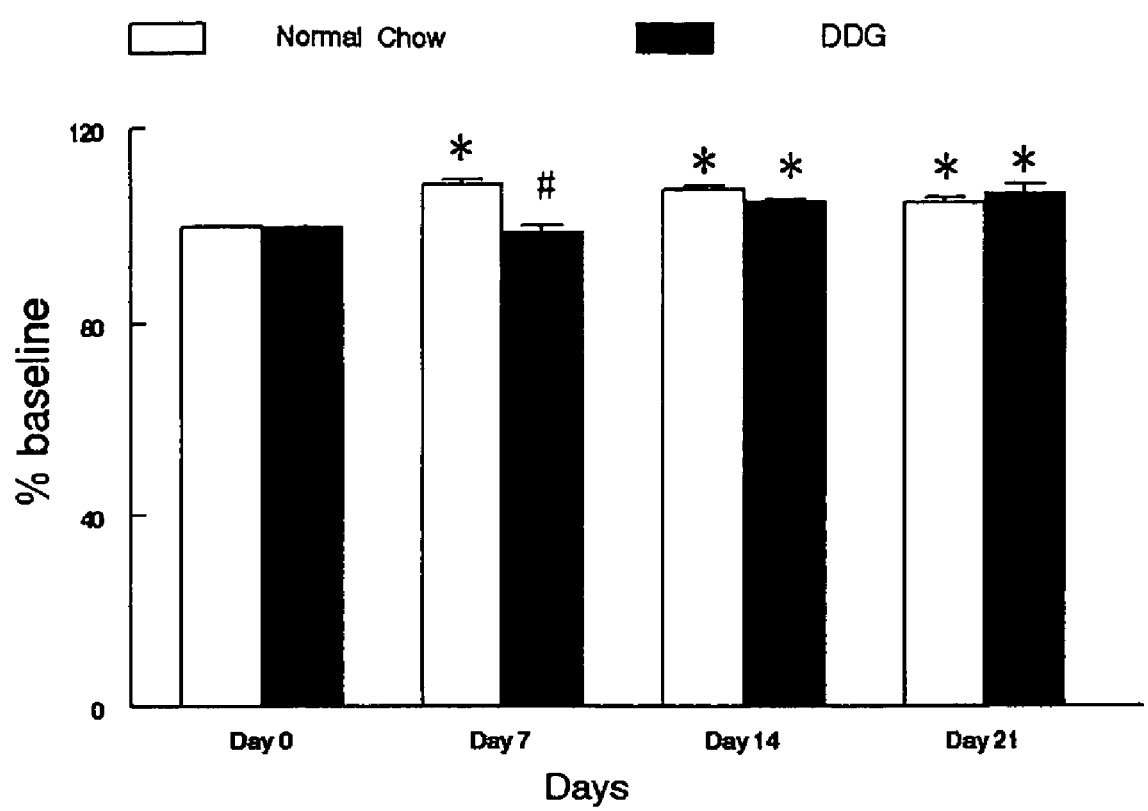
FIG. 3—is a bar graph showing change in body weight of rats fed normal chow (control, □), and rats fed DDG (DDG, ■) (N=3). *p 0.05 as compared to day zero values of respective fed group. #p 0.05 as compared to control values at that time point. Data was analysed using one-way analysis variance (ANOVA) followed by a post-hoc Student Newman Keul's test.
Figure 4:
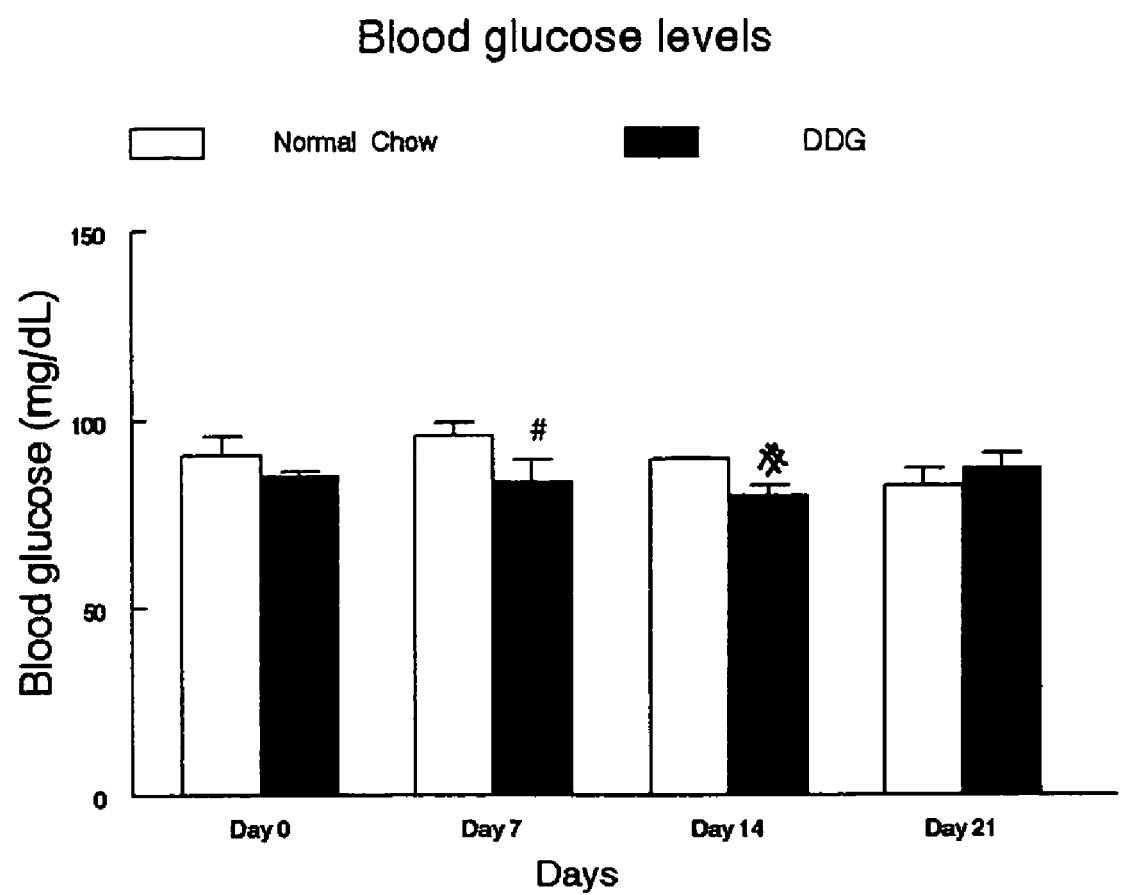
FIG. 4 is a bar graph showing blood glucose levels of rats fed normal chow (control, □), and rats fed DDG (DDG, ■) (N=3). #p 0.05 as compared to control values at that time point. Data was analysed using one-way analysis variance (ANOVA) followed by a post-hoc Student Newman Keul's test.

Referring to the accompanying tables and figures, rats were fed a diet of normal chow (control) or DDG. As can be seen in Table 1 and FIG. 1, initially, water intake by the DDG-fed rats was lower than that of the control rats, but increased to levels at or above that of the control rats within 3 days. Similarly, as can be seen in Table 2 and FIG. 2, food intake of DDG-fed rats was initially lower than that of control rats but increased to levels at or above that observed for control rats within 3 days. As can be seen in FIG. 3, the change in body weight of DDG-fed rats was noticeably lower than that of the control-fed rats after 7 days, slightly lower after 14 days and in fact slightly higher after 21 days. Referring to FIG. 4, the blood glucose levels of DDG-fed rats were lower compared to the control-fed rats at days 0, 7 and 14. This suggests that DDG has the ability to decrease blood sugar, which in turn further supports the effectiveness of administering DDG as a treatment for diabetes.

Taken together, these data clearly indicate that feeding animals a diet of DDG had no longer term negative effects on water intake, food intake, or change in body weight.

Figure 5:
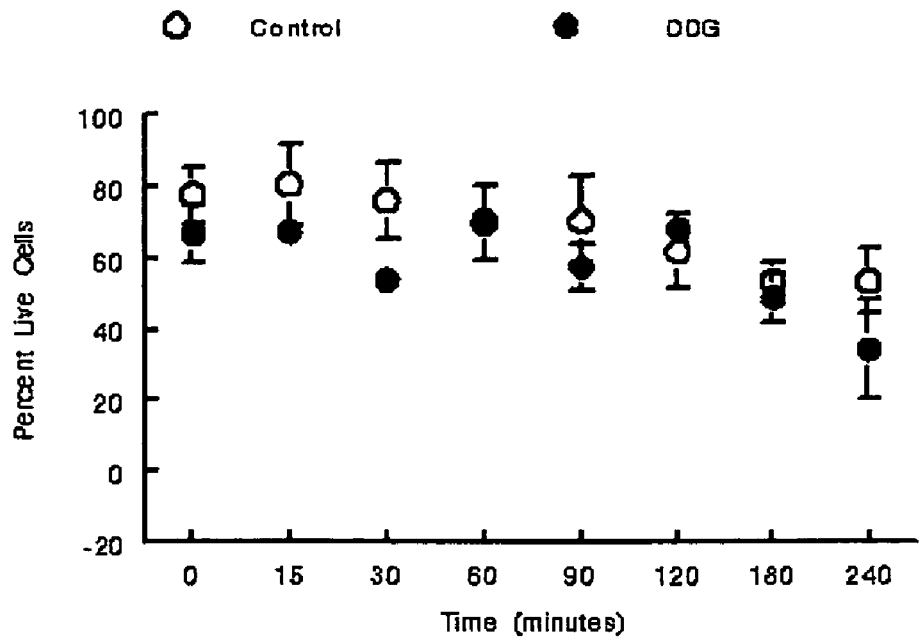
FIG. 5 (A) shows the percent live adult rat ventricular myocytes (AVRM) without ischemia (control, ○; DDG, ●); (B) shows the effect of ischemia (mineral oil) on ARVMs obtained from normal fed (normal chow, control, △) and DDG-fed (DDG, ▲) rats. * p 0.05 Vs. control (ischemia to ARVM obtained from normal fed rats) at corresponding time point. Data was analysed using one-way analysis variance (ANOVA) followed by a post-hoc Student Newman Keul's test.
Figure 5:
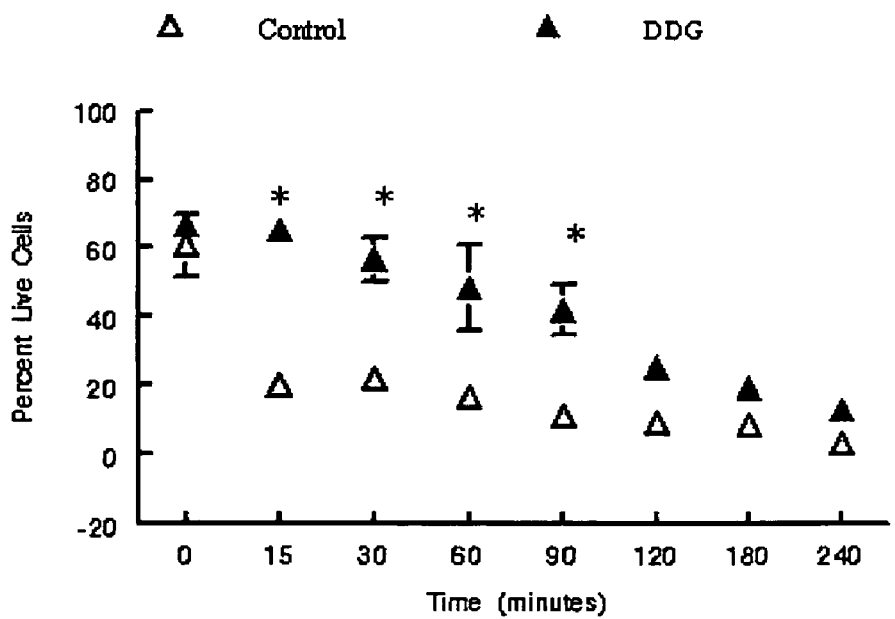

However, as shown in FIG. 5, DDG has the surprising effect of protecting adult rat ventricular myocytes from cell death due to ischemia. Specifically, as can be seen in FIG. 5(B), incubation of ARVMs from control rats in mineral oil resulted in a marked decrease in cell survival, compared to a gradual decrease in survival over time as seen in FIG. 5(A). However, ARVMs from rats fed DDG do not show a marked decrease in cell survival, but rather show a survival curve that is remarkably similar to that seen without mineral oil treatment (see FIG. 5B vs FIG. 5A).

While the preferred embodiments of the invention have been described above, it will be recognized and understood that various modifications may be made therein, and the appended claims are intended to cover all such modifications which may fall within the spirit and scope of the invention.

TABLE 1

Daily water intake (ml) in control (normal chow) and DDG fed rats (N = 3)

| Day | Control | DDG |
| --- | --- | --- |
| 1 | 53.33 ± 1.66 | 26.66 ± 1.66 |
| 2 | 50 ± 5 | 38.33 ± 4.40 |
| 3 | 43.33 ± 3.33 | 52.5 ± 2.5 |

TABLE 1-continued

Daily water intake (ml) in control (normal chow) and DDG fed rats (N = 3)

| Day | Control | DDG |
|---|---|---|
| 4 | 46.66 ± 1.66 | 53.33 ± 3.33 |
| 5 | 46.66 ± 1.66 | 50 ± 2.88 |
| 6 | 50 ± 0 | 56 ± 2.081 |
| 7 | 50 ± 2.88 | 51.66 ± 1.66 |
| 8 | 56.66 ± 4.40 | 59.16 ± 4.63 |
| 9 | 51.66 ± 4.40 | 55 ± 2.88 |
| 10 | 48.33 ± 1.66 | 54.16 ± 2.20 |
| 11 | 48.33 ± 3.33 | 60 ± 0 |
| 12 | 48.33 ± 3.33 | 53.33 ± 1.66 |
| 13 | 50 ± 2.886 | 58.33 ± 3.33 |
| 14 | 50 ± 2.88 | 53.33 ± 1.66 |
| 15 | 51.66 ± 1.66 | 63.33 ± 3.33 |
| 16 | 55 ± 2.886 | 55 ± 2.88 |
| 17 | 51.66 ± 1.66 | 58.33 ± 4.40 |
| 18 | 48.33 ± 1.66 | 55 ± 0 |
| 19 | 55 ± 2.88 | 56.66 ± 3.33 |
| 20 | 46.66 ± 3.33 | 51.66 ± 3.33 |
| 21 | 55 ± 0 | 58.33 ± 0.83 |

TABLE 2

Daily food intake (gm/day) in control (normal chow fed) and DDG fed rats (N = 3).

| Day | Control | DDG |
|---|---|---|
| 1 | 24.61 ± 0.36 | 9.08 ± 4.23 |
| 2 | 25.69 ± 1.79 | 14.89 ± 2.29 |
| 3 | 23.76 ± 0.84 | 22.91 ± 0.87 |
| 4 | 24.42 ± 0.76 | 24.712 ± 1.30 |
| 5 | 24.52 ± 1.21 | 24.17 ± 2.20 |
| 6 | 24.61 ± 1.44 | 23.35 ± 0.86 |
| 7 | 24.96 ± 1.32 | 25.73 ± 1.74 |
| 8 | 23.08 ± 2.36 | 25.49 ± 1.66 |
| 9 | 26.12 ± 1.54 | 22.88 ± 1.15 |
| 10 | 23.08 ± 1.49 | 25.82 ± 1.28 |
| 11 | 24.57 ± 0.35 | 24.75 ± 1.59 |
| 12 | 22.81 ± 1.82 | 25.81 ± 1.57 |
| 13 | 23.58 ± 1.80 | 24.51 ± 0.51 |
| 14 | 26.63 ± 1.45 | 23.02 ± 2.12 |
| 15 | 23.21 ± 0.97 | 27.76 ± 0.85 |
| 16 | 26.37 ± 0.69 | 23.79 ± 1.42 |
| 17 | 24.70 ± 0.43 | 27.57 ± 1.54 |
| 18 | 23.71 ± 0.40 | 25.40 ± 1.43 |
| 19 | 28.33 ± 1.87 | 26.63 ± 1.56 |
| 20 | 22.93 ± 1.69 | 25.22 ± 1.12 |
| 21 | 26.81 ± 2.23 | 25.59 ± 1.15 |

The invention claimed is:

1. A method for treating ischaemia in an animal subjected to ischeamia comprising:
   protecting myocytes in said animal from cell death due to ischaemia by administering to said animal a food portion comprising an effective amount of distiller's grain.

2. The method according to claim 1 wherein the distiller's grain is dry distiller's grain.

3. The method according to claim 1 wherein the distiller's grain is wet distiller's grain.

4. The method according to claim 1 wherein the animal is a livestock animal grown for meat.

5. The method according to claim 1 wherein the distiller's grain is administered as a bakery product.

6. The method according to claim 1 wherein the distiller's grain is administered as a cereal product.

7. The method according to claim 1 wherein the distiller's grain is administered as a breakfast or energy bar.

8. The method according to claim 1 wherein the animal is a human.

* * * * *